United States Patent [19]

Lesher et al.

[11] Patent Number: 4,590,194

[45] Date of Patent: May 20, 1986

[54] 3-[METHYL OR DIMETHYL)AMINO]-6-(PYRIDINYL)-PYRIDAZINES AND THEIR CARDIOTONIC USE

[75] Inventors: George Y. Lesher, Schodack; William B. Dickinson, Albany, both of N.Y.

[73] Assignee: Sterling Drug Inc., New York, N.Y.

[21] Appl. No.: 308,413

[22] Filed: Oct. 5, 1981

[51] Int. Cl.$^4$ .................. A61K 31/44; C07D 213/84; C07D 213/74
[52] U.S. Cl. ..................................... 514/247; 544/238
[58] Field of Search .................... 544/238; 424/250

[56] References Cited

U.S. PATENT DOCUMENTS

| 3,462,432 | 8/1969 | Gall et al. | 544/238 |
| 4,011,220 | 3/1977 | Kropp et al. | 544/239 |
| 4,072,746 | 2/1978 | Lesher et al. | 546/257 |
| 4,251,658 | 2/1981 | Szilágyi et al. | 544/238 |
| 4,304,775 | 12/1981 | Lesher et al. | 424/250 |
| 4,313,951 | 2/1982 | Lesher et al. | 424/263 |

FOREIGN PATENT DOCUMENTS

| 1108 | 3/1979 | European Pat. Off. | 424/250 |
| 2003461 | 8/1971 | Fed. Rep. of Germany | 544/236 |
| 19987 | 2/1979 | Japan . | |

OTHER PUBLICATIONS

Haginiwa et al., [Yakugaku Zasshi, 98 (1), 67–71 (1978); Chem. Abstrs. 88, 170,096v (1978)].

Cheesman et al, "Basicity of Pyridazine Derivatives", *J. Chem. Soc., Perkins Trans.* 2 (1972), pp. 392–394.

*Primary Examiner*—Donald G. Daus
*Assistant Examiner*—G. Hendricks
*Attorney, Agent, or Firm*—Robert K. Bair; B. Woodrow Wyatt; Paul E. Dupont

[57] ABSTRACT

3-(NB)-4-Q-6-PY-pyridazines (I) or salts thereof, which are useful as cardiotonics, are prepared by reacting a 3-halo-4-Q-6-PY-pyridazine with an amine, H-NB, to produce I, where PY is 4- or 3-pyridinyl or 4- or 3-pyridinyl having one or two lower-alkyl substituents and Q is cyano when NB is NHCH$_3$ or N(CH$_3$)$_2$, or Q is carbamyl when NB is NHCH$_3$, or Q is hydrogen when NB is N(CH$_3$)$_2$. Cardiotonic use of said 3-(NB)-4-Q-6-PY-pyridazines or salts is shown.

7 Claims, No Drawings

3-[METHYL OR DIMETHYL)AMINO]-6-(PYRIDINYL)PYRIDAZINES AND THEIR CARDIOTONIC USE 6-(4-Pyridinyl)-3-pyridazinol, tautomeric with 6-(4-pyridinyl)-3(2H)-pyridazinone, and its preparation from 4,5-dihydro-6-(4-pyridinyl)-3-pyridazinol are disclosed and claimed in copending application Ser. No. 144,576, filed Apr. 28, 1980 and now U.S. Pat. No. 4,304,777, issued Dec. 8, 1981, a continuation-in-part of its copending application Ser. No. 71,065, filed Aug. 30, 1979, and now abandoned. Also shown and claimed is the use of 6-(4-pyridinyl)-3-pyridazinol as a cardiotonic.

3-Hydrazino-6-(4-pyridinyl)pyridazine and its use as a cardiotonic are disclosed and claimed in copending application Ser. No 173,004, filed July 28, 1980 and now U.S. Pat. No. 4,304,775, issued Dec. 8, 1981, a continuation-in-part of its copending application Ser. No. 103,192, filed Dec. 13, 1979, and now abandoned.

3-Chloro-6-(4-pyridinyl)pyridazine and its conversion to 3-hydrazino-6-(4-pyridinyl)pyridazine are disclosed and claimed in copending application Ser. No. 238,229, filed Feb. 26, 1981 as a division of said application Ser. No. 173,004.

4-(Carbamyl, aminocarbamyl or lower-carbalkoxy)-6-(pyridinyl)-3(2H)-pyridazinones and their cardiotonic use are disclosed and claimed in copending application Ser. No. 144,697, filed Apr. 28, 1980 and now U.S. Pat. No. 4,304,776, issued Dec. 8, 1981.

Processes for preparing 2-alkyl-4-(carbamyl, carboxy, aminocarbamyl or lower-carbalkoxy)-6-(pyridinyl)-3-(2H)-pyridazinones and intermediates therefor are disclosed and claimed in copending application Ser. No. 238,483, filed Feb. 26, 1981 and now U.S. Pat. No. 4,338,446, issued July 6, 1982, a division of said application Ser. No. 144,697.

BACKGROUND OF THE INVENTION (a) Field of the Invention

This invention relates to 3-amino-6-(pyridinyl)-pyridazines, useful as cardiotonic agents, to their preparation, and to their use as cardiotonic agents.

(b) Description of the Prior Art

Haginiwa et al. [Yakugaku Zasshi 98 (1), 67–71 (1978); Chem. Abstrs. 88, 170,096 v 1978)] disclose the reaction of 3(2H)-pyridazinone with pyridine 1-oxide and platinized Pd-C catalyst to produce 6-(2-pyridinyl)-3(2H)-pyridazinone.

The Yoshitomi Pharmaceutical Ind., Ltd. Japanese Patent Application Disclosure No. 19,987/79, published Feb. 15, 1979 and based on application No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)-propanoic acid [same as γ-oxo-γ-(4-pyridinyl)butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and antithrombus agents because they have pharmacological actions such as hypotensive, blood platelet coagulation-inhibitory and membrane-stabilizing actions, but also as intermediates for the synthesis of such medicines".

SUMMARY OF THE INVENTION

In a composition of matter aspect, the invention resides in 3-(NB)-4-Q-6-PY-pyridazines (I) or acid-addition salts thereof, useful as cardiotonic agents, where NB, Q and PY are defined hereinbelow.

In the process aspect the invention comprises reacting a 3-halo-4-Q-6-PY-pyridazine with an amine of the formula H-NB to produce said 3-(NB)-4-Q-6-PY-pyridazines (I).

In a composition aspect, the invention resides in a cardiotonic composition for increasing cardiac contractility, said composition comprising a pharmaceutically acceptable inert carrier and, as the active component thereof, a cardiotonically effective amount of said 3-(NB)-4-Q-6-PY-pyridazine (I) or pharmaceutically acceptable acid-addition salt thereof.

In a method aspect, the invention relates to a method for increasing cardiac contractility in a patient requiring such treatment which comprises administering orally or parenterally in a solid or liquid dosage form to such patient a cardiotonically effective amount of said 3-(NB)-4-Q-6-PY-pyridazine or pharmaceutically acceptable acid-addition salt thereof.

DETAILED DESCRIPTION INCLUSIVE OF PREFERRED EMBODIMENTS

In a composition of matter aspect the invention resides in a 3-(NB)-4-Q-6-PY-pyridazine having formula I

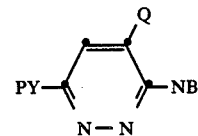

or acid-addition salt thereof, where PY is 4- or 3-pyridinyl or 4- or 3-pyridinyl having one or two lower-alkyl substituents and Q is cyano when NB is NHCH$_3$ or N(CH$_3$)$_2$, or Q is carbamyl when NB is NHCH$_3$, or Q is hydrogen when NB is N(CH$_3$)$_2$. The compounds of formula I are useful as cardiotonic agents, as determined by standard cardiotonic evaluation procedures.

In a process aspect the invention resides in the process which comprises reacting a 3-halo-4-Q-6-PY-pyridazine with an amine of the formula, H—NB to produce the compound of formula I where Q, PY and NB have the meanings given for formula I and halo is chloro or bromo, preferably chloro.

A composition aspect of the invention resides in the cardiotonic composition for increasing cardiac contractility, said composition comprising a pharmaceutically acceptable inert carrier and, as the active component thereof, a cardiotonically effective amount of 3-(NB)-4-Q-6-PY-pyridazine of formula I where NB, Q and PY are defined as in formula I, or pharmaceutically acceptable acid-addition salt thereof.

In a method aspect, the invention resides in the method for increasing cardiac contractility in a patient requiring such treatment which comprises administering orally or parenterally in a solid or liquid dosage form to such patient a cardiotonically effective amount of 3-(NB)-4-Q-6-PY-pyridazine where NB, Q and PY are defined as in formula I, or pharmaceutically acceptable acid-addition salt thereof.

The term "lower-alkyl" as used herein, e.g., as a substituent for PY means alkyl radicals having from one to six carbon atoms which can be arranged as straight or branched chains, illustrated by methyl, ethyl, n-propyl, isopropyl, n-butyl, 2-butyl, isobutyl, n-pentyl, n-hexyl, and the like.

The symbol PY as used herein, e.g., as the 6-substituent in the compounds having formula I, means 4- or 3-pyridinyl or 4- or 3-pyridinyl having one or two "lower-alkyl" substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The compounds of the invention having formula I are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, which give the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, and by the correspondence of calculated and found values for the elementary analyses.

The manner of making and using the instant invention will now be generally described so as to enable a person skilled in the art of pharmaceutical chemistry to make and use the same, as follows.

The intermediate 3-halo-4-Q-6-PY-pyridazines where Q is carbamyl are prepared by reacting 2,3-dihydro-3-oxo-6-PY-4-pyridazinecarboxylic acid with a halogenating agent, preferably phosphorus oxychloride, to produce 3-halo-6-PY-4-pyridazinecarboxylic acid halide and then heating said acid halide with ammonia in a suitable inert solvent, e.g., acetonitrile, to produce 3-halo-6-PY-4-pyridazinecarboxamide. Other halogenating agents include phenylphosphonic dichloride.

The intermediate 3-halo-4-Q-6-PY-pyridazines where Q is cyano are conveniently prepared by reacting the corresponding 3-halo-6-PY-4-pyridazinecarboxamide with phosphorus oxychloride or phenyl phosphonic dichloride, preferably heating the reactants on a steam bath. It was found that the addition of a small quantity of dimethylformamide, although not necessary, helped to expedite the reaction.

The intermediate 3-halo-6-PY-pyridazine is conveniently prepared by heating 6-PY-3(2H)-pyridazinone with a chlorinating agent, preferably phosphorus oxychloride on a steam bath. Alternatively, other chlorinating agents that can be used are phosphorus trichloride and phenylphosphonic dichloride ($C_6H_5POCl_2$). The reaction can be run by heating the reactants at about 70° to 120° C., preferably about 90°–100° C., in the absence or presence of a suitable solvent, e.g., dioxane, benzene, toluene, or the like.

The reaction of a 3-halo-4-Q-6-PY-pyridazine with H-NB to produce the corresponding 3-(NB)-4-Q-6-PY-pyridazine is carried out by heating the reactants in a suitable inert solvent at about 60° C. to about 100° C., preferably at 75° C. to about 85° C. The reaction is conveniently run in refluxing ethanol or acetonitrile. Other suitable solvents include dioxane, tetrahydrofuran, other lower-alkanols, e.g., methanol, isopropyl alcohol, n-butanol, and the like.

A. 3-HALO-4-Q-6-PY-PYRIDAZINES

A-1. 3-Chloro-6-(4-pyridinyl)-4-pyridazinecarboxamide

A mixture containing 18 g. of 2,3-dihydro-3-oxo-6-(4-pyridinyl)pyridazinecarboxylic acid and 160 ml. of phosphorus oxychloride was heated with stirring on a steam bath for twenty hours and then evaporated in vacuo to dryness. The residue was boiled with 1 liter of acetonitrile and the resulting solution filtered. The filtrate was added to 200 ml. of acetonitrile saturated with dry ammonia whereupon a white precipitate separated. Dry ammonia was bubbled into the mixture for thirty minutes. The precipitate was then collected by filtration, washed with water, dried in a vacuum oven over $P_2O_5$, stirred with 20 ml. of 10% aqueous sodium bicarbonate solution, collected again, washed with water and dried in a vacuum oven over $P_2O_5$ at 45° C. overnight to yield 4.6 g. of 3-chloro-6-(4-pyridinyl)-4-pyridazinecarboxamide, m.p. >300° C.

A-2. 3-Chloro-6-(4-pyridinyl)-4-pyridazinecarbonitrile

A mixture containing 22 g. of 3-chloro-6-(4-pyridinyl)-4-pyridazinecarboxamide, 180 ml. of phosphorus oxychloride and 12 drops of dimethylformamide was heated on a steam bath with stirring for twenty-one hours. The excess phosphorus oxychloride was evaporated off in vacuo using a rotary evaporator. The residue was dissolved by gently warming it with about 155 ml. of water, cooling the resulting solution and then carefully adding solid potassium bicarbonate in small portions until vigorous evolution of carbon dioxide ceased. The pH of the mixture was approximately 8.5. The brown solid was collected, rinsed with water and dried in vacuo (10 mm) over $P_2O_5$ at 25° C. The solid (18.9 g.) was warmed gently with 200 ml. of acetonitrile to effect dissolution; the solution containing a small amount of insoluble material was treated with decolorizing charcoal and filtered through diatomaceous earth (filtration slow). The filter cake was taken up in more acetonitrile (150 ml.), the mixture warmed on a steam bath and filtered. The acetonitrile filtrates were combined and evaporated using a rotary evaporator. The resulting residue was allowed to stand and dry to yield 17 g. of 3-chloro-6-(4-pyridinyl)-4-pyridazinecarbonitrile (caution-sternutator).

A-3. 3-Chloro-6-(4-pyridinyl)pyridazine

In a 50 ml. round bottom flask equipped with a magnetic stirrer, a reflux condenser and drying tube was placed a mixture of 2 g. of 6-(4-pyridinyl)-3(1H)-pyridazinone and 20 ml. of phosphorus oxychloride. The mixture was refluxed on a steam bath for 21 hours. The resulting solution was heated in vacuo to remove the excess phosphorus oxychloride and volatile reaction products and the resulting oily material was chilled in an ice bath and stirred with about 20 ml. of water. The resulting solution was filtered through diatomaceous earth and the filtrate was basified with sodium bicarbonate. The solid which separated was collected, recrystallized from absolute ethanol and dried in a vacuum oven over $P_2O_5$ for 17 hours to yield 1.6 g. of 3-chloro-6-(4-pyridinyl)pyridazine, m.p. 172°–173° C.

Following the procedure described in Example A-1 but using in place of 2,3-dihydro-3-oxo-6-(4-pyridinyl)-4-pyridazinecarboxylic acid a molar equivalent quantity of the appropriate 2,3-dihydro-3-oxo-6-PY-3-pyridazinecarboxylic acid, it is contemplated that there can be obtained the corresponding 3-chloro-6-PY-4-pyridazinecarboxamides of Examples A-4 thru A-8.

A-4. 3-Chloro-6-(3-pyridinyl)-4-pyridazinecarboxamide.
A-5. 3-Chloro-6-(2-methyl-3-pyridinyl)-4-pyridazinecarboxamide.
A-6. 3-Chloro-6-(5-methyl-3-pyridinyl)-4-pyridazinecarboxamide.
A-7. 3-Chloro-6-(3-ethyl-4-pyridinyl)-4-pyridazinecarboxamide.
A-8. 3-Chloro-6-(2,6-dimethyl-4-pyridinyl)-4-pyridazinecarboxamide.

Following the procedure described in Example A-2 but using in place of 3-chloro-6-(4-pyridinyl)-4-pyridazinecarboxamide a molar equivalent quantity of the appropriate 3-chloro-6-PY-3-pyridazinecarboxamide, it is contemplated that there can be obtained the corresponding 3-chloro-6-PY-3-pyridazinecarbonitriles of Examples A-9 thru A-13.
A-9. 3-Chloro-6-(3-pyridinyl)-4-pyridazinecarbonitrile.
A-10. 3-Chloro-6-(2-methyl-3-pyridinyl)-4-pyridazinecarbonitrile.
A-11. 3-Chloro-6-(5-methyl-3-pyridinyl)-4-pyridazinecarbonitrile.
A-12. 3-Chloro-6-(3-ethyl-4-pyridinyl)-4-pyridazinecarbonitrile.
A-13. 3-Chloro-6-(2,6-dimethyl-4-pyridinyl)-4-pyridazinecarbonitrile.

Following the procedure described in Example A-3 but using in place of 6-(4-pyridinyl)-3(2H)-pyridazinone a molar equivalent quantity of the appropriate 6-PY-3(2H)-pyridazinone, it is contemplated that there can be obtained the corresponding 3-chloro-6-PY-pyridazines of Examples A-14 thru A-18.
A-14. 3-Chloro-6-(3-pyridinyl)pyridazine.
A-15. 3-Chloro-6-(2-methyl-3-pyridinyl)pyridazine.
A-16. 3-Chloro-6-(5-methyl-3-pyridinyl)pyridazine.
A-17. 3-Chloro-6-(3-ethyl-4-pyridinyl)pyridazine.
A-18. 3-Chloro-6-(2,6-dimethyl-4-pyridinyl)pyridazine.

B. 3-(NB)-4-Q-6-PY-PYRIDAZINES

B-1. 3-Methylamino-6-(4-pyridinyl)-4-pyridazinecarboxamide

Into 200 ml. of absolute ethanol chilled in an ice bath was bubbled methylamine for about twenty minutes. To the ethanolic methylamine solution was added 7.1 g. of 3-chloro-6-(4-pyridinyl)-4-pyridazinecarboxamide and the resulting reaction mixture was refluxed with stirring for six hours. The solvent was distilled off in vacuo and the residue was mixed and stirred first with water and filtered, and then with ethanol and filtered. The solid was dried at 45° C. in a vacuum oven over $P_2O_5$ to yield 8.4 g. of 3-methylamino-6-(4-pyridinyl)-4-pyridazinecarboxamide, m.p. 275°–276° C.

Acid-addition salts of 3-methylamino-6-(4-pyridinyl)-4-pyridazinecarboxamide are conveniently prepared by adding to a mixture of 1 g. of 3-methylamino-6-(4-pyridinyl)- 4-pyridazinecarboxamide in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-methylamino-6-(4-pyridinyl)-4-pyridazinecarboxamide and the appropriate acid, e.g., lactic acid or hydrochloric acid, to prepare respectively the lactate or hydrochloride salt of 3-methylamino-6-(4-pyridinyl)-4-pyridazinecarboxamide in aqueous solution.

B-2. 3-Methylamino-6-(4-pyridinyl)-4-pyridazinecarbonitrile

To a solution containing 5.0 g. of 3-chloro-6-(4-pyridinyl)-4-pyridazinecarbonitrile in 35 ml. of absolute ethanol was added 35 ml. of 27% (w/w) methylamine in ethanol whereupon a mildly exothermic reaction ensued with the intermediate 3-chloro compound dissolving and the product separating. The reaction mixture was allowed to stand at ambient temperature for about forty minutes with occasional shaking. The precipitated product was collected, rinsed with ethanol, air-dried and then dried at 65° C. over $P_2O_5$ at 10 mm. to yield 4.04 g. of 3-methylamino-6-(4-pyridinyl)-4-pyridazinecarbonitrile, m.p. 242°–265° C. with decomposition.

Acid-addition salts of 3-methylamino-6-(4-pyridinyl)-4-pyridazinecarbonitrile are conveniently prepared by adding to a mixture of 1 g. of 3-methylamino-6-( 4-pyridinyl)-4-pyridazinecarbonitrile in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-methylamino-6-(4-pyridinyl)-4-pyridazinecarbonitrile and the appropriate acid, e.g., lactic acid or hydrochloric acid, to prepare respectively the lactate or hydrochloride salt of 3-methylamino-6-(4-pyridinyl)-4-pyridazinecarbonitrile in aqueous solution.

B-3. 3-Dimethylamino-6-(4-pyridinyl)-4-pyridazinecarbonitrile

To a mixture containing 10 g. of 3-chloro-6-(4-pyridinyl)-4-pyridazinecarbonitrile and 70 ml. of absolute ethanol was added with stirring 15 ml. of 40% (w/v) aqueous dimethylamine and the mixture was stirred for about 15 minutes at ambient temperature, next gently warmed on a steam bath, and then heated to boiling on a hot plate. The reaction mixture was next cooled in an ice bath. The separated solid was collected, rinsed with a little ethanol, air-dried and then dried at 65° C. over $P_2O_5$ at 10 mm. to yield 8.65 g. of 3-dimethylamino-6-(4-pyridinyl)-4-pyridazinecarbonitrile, m.p. 204°–206° C.

Acid-addition salts of 3-dimethylamino-6-(4-pyridinyl)-4-pyridazinecarbonitrile are conveniently prepared by adding to a mixture of 1 g. of 3-dimethylamino-6-( 4-pyridinyl)-4-pyridazinecarbonitrile in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-dimethylamino-6-(4-pyridinyl)-4-pyridazinecarbonitrile and the appropriate acid, e.g., lactic acid or hydrochloric acid, to prepare respectively the lactate or hydrochloride salt of 3-dimethylamino-6-(4-pyridinyl)-4-pyridazinecarbonitrile in aqueous solution.

B-4. 3-Dimethylamino-6-(4-pyridinyl)pyridazine

A mixture containing 30 g. of dimethylamine in 250 ml. of methanol and 10 g. of 3-chloro-6-(4-pyridinyl)-pyridazine was autoclaved at 100° C. for twenty-four hours and then evaporated to dryness to remove the solvent and excess dimethylamine. To the cooled solid residue was added 100 ml. of water followed by 10 g. of potassium bicarbonate; the aqueous mixture was mixed well, allowed to stand for ten minutes and the tan solid collected, pressed dry, rinsed twice with small portions of water and air-dried to yield 9.0 g. of product, m.p. 198°–202° C. The product was combined with 11.3 g. of product prepared similarly in other runs and the combined product was dissolved in 450 ml. of hot acetonitrile and decolorizing charcoal added; the hot mixture was filtered; and, the filtrate was concentrated to a volume of about 225 ml. and chilled in an ice bath. The tan solid was collected, rinsed with acetonitrile, air-dried briefly and then dried at 65° C. over $P_2O_5$ at 10 mm. for eighteen hours to yield 11.7 g. of 3-dimethylamino-6-(4-pyridinyl)-pyridazine, m.p. 201.5°–203° C.

Acid-addition salts of 3-dimethylamino-6-(4-pyridinyl)pyridazine are conveniently prepared by adding to a mixture of 1 g. of 3-dimethylamino-6-(4-pyridinyl)pyridazine in about 20 ml. of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 3-dimethylamino-6-(4-pyridinyl)pyridazine and the appropriate acid, e.g., lactic acid or hydrochloric acid, to prepare respectively the lactate or hydrochloride salt of 3-dimethylamino-6-(4-pyridinyl)pyridazine in aqueous solution.

Following the procedure described in Example B-1 but using in place of 3-chloro-6-(4-pyridinyl)-4-pyridazinecarboxamide a molar equivalent quantity of the appropriate 3-chloro-6-PY-3-pyridazinecarboxamide, it is contemplated that there can be obtained the corresponding 3-methylamino-6-PY-4-pyridazinecarboxamides of Examples B-5 thru B-9.

B-5. 3-Methylamino-6-(3-pyridinyl)-4-pyridazinecarboxamide.
B-6. 3-Methylamino-6-(2-methyl-3-pyridinyl)-4-pyridazinecarboxamide.
B-7. 3-Methylamino-6-(5-methyl-3-pyridinyl)-4-pyridazinecarboxamide.
B-8. 3-Methylamino-6-(3-ethyl-4-pyridinyl)-4-pyridazinecarboxamide.
B-9. 3-Methylamino-6-(2,6-dimethyl-4-pyridinyl)-4-pyridazinecarboxamide.

Following the procedure described in Example B-2 but using in place of 3-chloro-6-(4-pyridinyl)-4-pyridazinecarbonitrile a molar equivalent quantity of the appropriate 3-chloro-6-PY-3-pyridazinecarbonitrile, it is contemplated that there can be obtained the corresponding 3-methylamino-6-PY-4-pyridazinecarbonitriles of Examples B-10 thru B-14.

B-10. 3-Methylamino-6-(3-pyridinyl)-4-pyridazinecarbonitrile.
B-11. 3-Methylamino-6-(2-methyl-3-pyridinyl)-4-pyridazinecarbonitrile.
B-12. 3-Methylamino-6-(5-methyl-3-pyridinyl)-4-pyridazinecarbonitrile.
B-13. 3-Methylamino-6-(3-ethyl-4-pyridinyl)-4-pyridazinecarbonitrile.
B-14. 3-Methylamino-6-(2,6-dimethyl-4-pyridinyl)-4-pyridazinecarbonitrile.

Following the procedure described in Example B-3 but using in place of 3-chloro-6-(4-pyridinyl)-4-pyridazinecarbonitrile a molar equivalent quantity of the appropriate 3-chloro-6-PY-4-pyridazinecarbonitrile, it is contemplated that there can be obtained the corresponding 3-dimethylamino-6-PY-4-pyridazinecarbonitriles of Examples B-15 thru B-19.

B-15. 3-Dimethylamino-6-(3-pyridinyl)-4-pyridazinecarbonitrile.
B-16. 3-Dimethylamino-6-(2-methyl-3-pyridinyl)-4-pyridazinecarbonitrile.
B-17. 3-Dimethylamino-6-(5-methyl-3-pyridinyl)-4-pyridazinecarbonitrile.

B-18. 3-Dimethylamino-6-(3-ethyl-4-pyridinyl)-4-pyridazinecarbonitrile.

B-19. 3-Dimethylamino-6-(2,6-dimethyl-4-pyridinyl)-4-pyridazinecarbonitrile.

Following the procedure described in Example B-4 but using-in place of 3-chloro-6-(4-pyridinyl)pyridazine a molar equivalent quantity of the appropriate 3-chloro-6-PY-pyridazine, it is contemplated that there can be obtained the corresponding 3-dimethylamino-6-PY-pyridazines of Examples B-20 thru B-24.

B-20. 3-Dimethylamino-6-(3-pyridinyl)pyridazine.

B-21. 3-Dimethylamino-6-(2-methyl-3-pyridinyl)-pyridazine.

B-22. 3-Dimethylamino-6-(5-methyl-3-pyridinyl)-pyridazine.

B-23. 3-Dimethylamino-6-(3-ethyl-4-pyridinyl)-pyridazine.

B-24. 3-Dimethylamino-6-(2,6-dimethyl-4-pyridinyl)-pyridazine.

The usefulness of the compounds of formula I, or pharmaceutically acceptable acid-addition salts thereof, as cardiotonic agents is demonstrated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated cat or guinea pig atria and papillary muscle procedure, the compounds of formula I or pharmaceutically acceptable acid-addition salts thereof at doses of 10, 30, 100 and/or 300 $\mu$g./ml., were found to cause significant increases, that is, greater than 25% (cat) or 30% (guinea pig) in papillary muscle force and significant increases, that is, greater than 25% (cat) or 30% (guinea pig), in right atrial force, while causing a lower percentage increase in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at said dose levels by this procedure in the cat test, the compound of Example B-1, namely, 3-methylamino-6-(4-pyridinyl)-4-pyridazinecarboxamide, was found to cause respective increases in papillary muscle force and right atrial force of 29% and 22% at 10 $\mu$g/ml., 53% and 32% at 30 $\mu$g/ml., 101% and 70% at 100 $\mu$g/ml. and 134% and 104% at 300 $\mu$g/ml. When tested by this procedure in the guinea pig test, the compound of Example B-2, namely, 3-methylamino-6-(4-pyridinyl)-4-pyridazinecarbonitrile, was found to cause respective increases in papillary muscle force and right atrial force of 50% and 33% at 10 $\mu$g/ml., 104% and 65% at 30 $\mu$g/ml. and 182% and 155% at 100 $\mu$g/ml.; the compound of Example B-3, namely, 3-dimethylamino-6-(4-pyridinyl)-4-pyridazinecarbonitrile, was found to cause respective increases in papillary muscle force and right atrial force of 30% and 19% at 10 $\mu$g/ml., 62% and 58% at 30 $\mu$g/ml. and 148% and 195% at 100 $\mu$g/ml.; and, the compound of Example B-4, namely, 3-dimethylamino-6-(4-pyridinyl)pyridazine, was found to cause respective increases in papillary muscle force and right atrial force of 46% and 59% at 100 $\mu$g/ml.

The present invention includes within its scope a cardiotonic composition comprising a pharmaceutically acceptable carrier and, as the active component thereof, the cardiotonic compound of formula I or pharmaceutically acceptable acid-addition salt thereof. The invention also includes within its scope the method for increasing cardiac contractility in a patient requiring such treatment which comprises administering to such patient a cardiotonically effective amount of the compound of formula I or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Compositions according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

They can be sterilized, for example, by filtration through a bacteria-retaining filter, by incorporation of sterilizing agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. A 3-(NB)-4-Q-6-PY-pyridazine having the formula

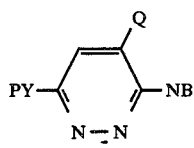

or acid-addition salt thereof, where PY is 4- or 3-pyridinyl or 4- or 3-pyridinyl having one or two lower-alkyl substituents where each lower-alkyl has from one to six carbon atoms which can be arranged as straight or branched chains and Q is cyano when NB is NHCH3 or N(CH3)2, or Q is carbamyl when NB is NHCH3, or Q is hydrogen when NB is N(CH3)2.

2. A compound according to claim 1 where PY is 4-pyridinyl, Q is cyano and NB is NHCH3.

3. A compound according to claim 1 where PY is 4-pyridinyl, Q is cyano and NB is N(CH3)2.

4. A compound according to claim 1 where PY is 4-pyridinyl, Q is hydrogen and NB is N(CH3)2.

5. A compound according to claim 1 where PY is 4-pyridinyl, Q is carbamyl and NB is NHCH3.

6. A cardiotonic composition for increasing cardiac contractility, said composition comprising a pharmaceutically acceptable inert carrier and, as the active component thereof, a cardiotonically effective amount of 3-(NB)-4-Q-6-PY-pyridazine of pharmaceutically acceptable acid-addition salt thereof where PY is 4- or 3-pyridinyl or 4- or 3-pyridinyl having one or two lower-alkyl substituents where each lower-alkyl has from one to six carbon atoms which can be arranged as straight or branched chains and Q is cyano when NB is NHCH3 or N(CH3)2, or Q is carbamyl when NB is NHCH3, or Q is hydrogen when NB is N(CH3)2.

7. The method for increasing cardiac contractility in a patient requiring such treatment which comprises administering orally or parenterally in a solid or liquid dosage form to such patient a cardiotonically effective amount of 3-(NB)-4-Q-6-PY-pyridazine or pharmaceutically acceptable acid-addition salt thereof, where PY is 4- or 3-pyridinyl or 4- or 3-pyridinyl having one or two lower-alkyl substituents where each lower-alkyl has from one to six carbon atoms which can be arranged as straight or branched chains and Q is cyano when NB is NHCH3 or N(CH3)2, or Q is carbamyl when NB is NHCH3, or Q is hydrogen when NB is N(CH3)2.

* * * * *